United States Patent
Wu (10) Patent No.: US 8,400,551 B2
(45) Date of Patent: Mar. 19, 2013

(54) HIGH RESOLUTION LABEL FREE IMAGING

(75) Inventor: Qi Wu, Painted Post, NY (US)

(73) Assignee: Corning Incorporated, Corning, NY (US)

(*) Notice: Subject to any disclaimer, the term of this patent is extended or adjusted under 35 U.S.C. 154(b) by 212 days.

(21) Appl. No.: 13/021,945

(22) Filed: Feb. 7, 2011

(65) Prior Publication Data

US 2011/0205422 A1 Aug. 25, 2011

Related U.S. Application Data

(60) Provisional application No. 61/306,627, filed on Feb. 22, 2010.

(51) Int. Cl.
*G02B 13/16* (2006.01)
*H04N 5/225* (2006.01)
(52) U.S. Cl. .......................... 348/335; 356/445; 356/422
(58) Field of Classification Search ............... 348/222.1, 348/335, 340, 345, 348; 356/445, 422, 82.05
See application file for complete search history.

(56) References Cited

U.S. PATENT DOCUMENTS

| | | | |
|---|---|---|---|
| 6,677,131 B2 | 1/2004 | Yuen | 435/29 |
| 7,175,980 B2 | 2/2007 | Qiu et al. | 435/4 |
| 7,495,768 B2 * | 2/2009 | Mori et al. | 356/445 |
| 2003/0099940 A1 * | 5/2003 | Empedocles et al. | 435/6 |
| 2005/0134860 A1 | 6/2005 | Chinowsky | 356/445 |
| 2010/0176307 A1 * | 7/2010 | Hell et al. | 250/459.1 |

FOREIGN PATENT DOCUMENTS

| | | |
|---|---|---|
| WO | 2008/094285 | 8/2008 |
| WO | 2008/106013 | 9/2008 |

* cited by examiner

*Primary Examiner* — Yogesh Aggarwal
(74) *Attorney, Agent, or Firm* — John L. Haack (57) ABSTRACT

An apparatus having an optical reader system and method for label-independent detection having improved spatial resolution of the reader, as defined herein. The system includes an optical configuration for interrogating a sensor on a microplate at an incident angle ($\theta_1$) of greater than 45°, and recording the image received from the contacted sensor with the image recorder, the image recorder being oriented with respect to the reflected beam at a reflected angle ($\theta_2$) of greater than about 5°, as further defined herein.

13 Claims, 7 Drawing Sheets

HIGH RESOLUTION LABEL FREE IMAGING

CLAIMING BENEFIT OF PRIOR FILED U.S. APPLICATION

This application claims the benefit of U.S. Provisional Ser. No. 61/306,627, filed on Feb. 22, 2010. The entire disclosure of any publication or patent document mentioned herein is incorporated by reference.

BACKGROUND

The disclosure generally relates to an apparatus and method for enhanced spatial resolution of an optical reader.

SUMMARY

The disclosure provides an apparatus and method for enhanced spatial resolution of an optical reader.

BRIEF DESCRIPTION OF THE DRAWING(S)

In embodiments of the disclosure.

DETAILED DESCRIPTION

Various embodiments of the disclosure will be described in detail with reference to drawings. Reference to various embodiments does not limit the scope of the invention, which is limited only by the scope of the claims attached hereto. Additionally, any examples set forth in this specification are not limiting and merely set forth some of the many possible embodiments for the claimed invention.

DEFINITIONS

"Incident angle ($\theta_1$)" or like term refers to the approximate angle formed between a collimated source beam (which contacts an optical sensor on the received microplate in the receptacle) and an orthogonal projection (normal or perpendicular) from the optical sensor on the received microplate.

"Reflected angle ($\theta_2$)" or like term refers to the approximate angle between the reflected beam from the optical sensor of the received microplate and incident on image recorder and the orthogonal projection (normal or perpendicular) from the plane of the image recorder.

"Biosensor," "sensor," or like term refers to an article, that in combination with appropriate apparatus, can detect a desired analyte or condition. A biosensor combines a biological component with a physicochemical detector component. A biosensor can typically consist of three parts: a biological component or element (such as tissue, microorganism, pathogen, cells, cell component, a receptor, and like entities, or combinations thereof), a detector element (operating in a physicochemical way such as optical, piezoelectric, electrochemical, thermometric, magnetic, or like manner), and a transducer associated with both components. In embodiments, the biosensor can convert a molecular recognition, molecular interaction, molecular stimulation, or like event occurring in a surface bound cell component or cell, such as a protein or receptor, into a detectable and quantifiable signal. A biosensor as used herein can include liquid handling systems which are static, dynamic, or a combination thereof. In embodiments of the disclosure, one or more biosensor can be incorporated into a micro-article. Biosensors are useful tools and some exemplary uses and configurations are disclosed, for example, in PCT Application No. PCT/US2006/013539 (Pub. No. WO 2006/108183), published Dec. 10, 2006, to Fang, Y., et al., entitled "Label-Free Biosensors and Cells," and U.S. Pat. No. 7,175,980. Biosensor-based cell assays having penetration depths, detection zones, or sensing volumes have been described, see for example, Fang, Y., et al. "Resonant waveguide grating biosensor for living cell sensing," *Biophys. J.*, 91, 1925-1940 (2006). Microfluidic articles are also useful tools and some exemplary uses, configurations, and methods of manufacture are disclosed, for example, in U.S. Pat. Nos. 6,677,131, and 7,007,709. U.S. Patent Publication 2007/0141231 and U.S. Pat. No. 7,175,980, disclose a microplate assembly and method. These documents are hereby incorporated by reference in their entirety.

The articles and methods of the disclosure are particularly well suited for biosensors based on label-independent detection (LID), such as for example an Epic® system or those based on surface plasmon resonance (SPR). The articles, and methods of the disclosure are also compatible with an alternative LID sensor, such as Dual Polarized Intereferometry (DPI). In embodiments, the biosensor system can comprise, for example, a swept wavelength optical interrogation imaging system for a resonant waveguide grating biosensor, an angular interrogation system for a resonant waveguide grating biosensor, a spatially scanned wavelength interrogation system, surface plasmon resonance system, surface plasmon resonance imaging, or a combination thereof.

Commonly owned and assigned copending U.S. Patent Application Publication 2007/0154356 (U.S. Ser. No. 11/436,923) discloses at para. [0042] an optically readable microplate having an attached mask with apertures. This document is hereby incorporated by reference in its entirety.

"About" modifying, for example, the quantity, dimension, process temperature, process time, and like values, and ranges thereof, employed in describing the embodiments of the disclosure, refers to variation in the numerical quantity that can occur, for example: through typical measuring and handling procedures used; through inadvertent error in these procedures; through differences in the manufacture, source, or quality of components and like considerations. The term "about" also encompasses amounts that differ due to aging of or environmental effects on components. The claims appended hereto include equivalents of these "about" quantities.

"Optional," "optionally," or like terms refer to the subsequently described event or circumstance can or cannot occur, and that the description includes instances where the event or circumstance occurs and instances where it does not. For example, the phrase "optional component" or like phrase means that the component can or can not be present and that the disclosure includes both embodiments including and excluding the component.

"Consisting essentially of" in embodiments refers, for example, to optical readers and associated components, to an assay, to method of using the assay to screen compounds, and to articles, devices, or any apparatus of the disclosure, and can include the components or steps listed in the claim, plus other components or steps that do not materially affect the basic and novel properties of the articles, apparatus, or methods of making and use of the disclosure, such as particular components, a particular light source or wavelength, a particular surface modifier or condition, or like structure, material, or process variable selected. Items that may materially affect the basic properties of the components or steps of the disclosure or that may impart undesirable characteristics to aspects of the disclosure include, for example, having a disfavored orientation of the radiation source or the image recorder.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, and "rt" for room temperature, "nm" for nanometers, and like abbreviations).

Specific and preferred values disclosed for components, times, operations, and like aspects, and ranges thereof, are for illustration only; they do not exclude other defined values or other values within defined ranges. The article, apparatus, and methods of the disclosure include those having any value or any combination of the values, specific values, more specific values, and preferred values described herein.

The Corning, Inc., Epic® system is a high throughput label free detection technology platform for studying bio-molecular interactions and live cells. A commercially available Epic® instrument can detect the average response of each biosensor in a microplate. Label free imaging methods continue to evolve and can now provide spatially resolved high content label free responses within each sensor (see for example, commonly owned and assigned U.S. Pat. No. 7,599,055, to Gollier et al., entitled "Swept wavelength imaging optical interrogation system and method for using same"). This document(s) is hereby incorporated by reference in its entirety.

The spatial resolution of the Epic® sensor has been limited by the decay length of the leakage wave ("leaky wave") in the grating coupler to about 220 micrometers. With normal ($\theta_1=0°$) incidence interrogation, the second order Bragg grating couples the degenerate forward and backward propagating waves and the resulting spatial resolution is improved to about 100 micrometers. In embodiments, the disclosure provides a method to improve the spatial resolution to less than about 10 micrometers. In embodiments, the improved spatial resolution can be realized without any redesign of the Epic® sensor.

In embodiments, the disclosure provides a method for high resolution label free imaging based on a conventional waveguide grating sensor. By interrogating the sensors at a high incident angle, for example greater than about 45°, the decay length of the leaky wave can be greatly reduced compared with near normal incidence of about $\theta_1=0°$. This brings the spatial resolution to well below 10 micrometers. The interrogation method provides dramatic improvements in spatial resolution.

In embodiments, the disclosure provides an apparatus and a method for improving spatial resolution of an optical reader for biochemical, live-cell, and like label-independent-detection (LID) assays.

The disclosure provides an optical reader apparatus, and a method of use having improved image spatial resolution.

Figure 7A:
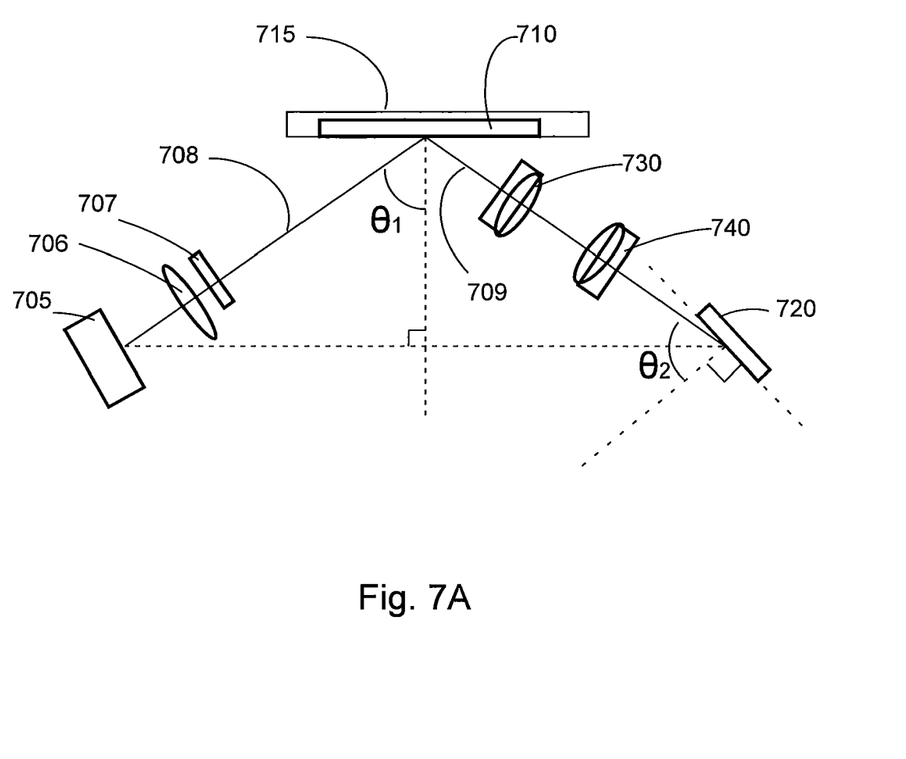
FIGS. 7A and 7B show, respectively, a schematic of an optical design for high-resolution label-free imaging of a sensor, and an exemplary prior art microplate having one or more sensors.
Figure 7B:
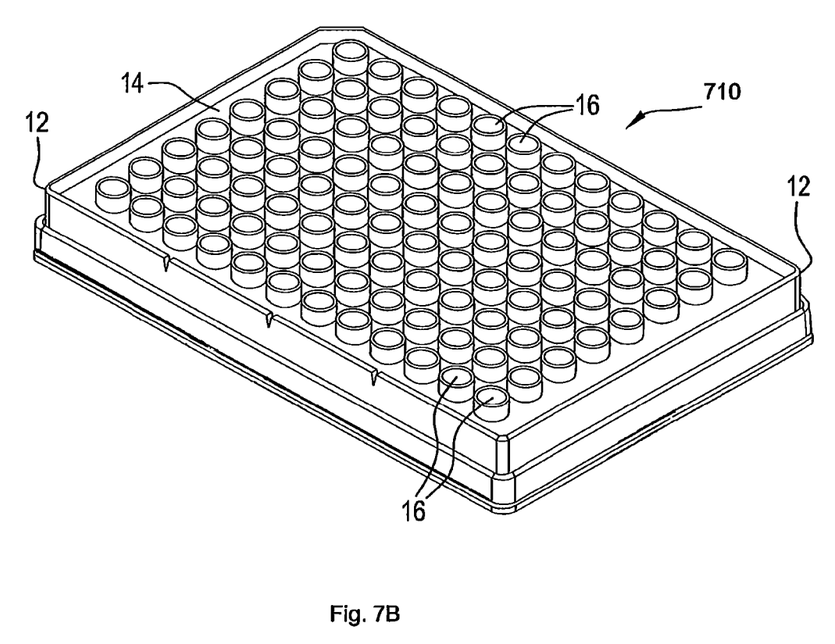

In embodiments, and referring to FIGS. 7A and 7B, the disclosure provides an apparatus for label free imaging comprising, for example:
  an optical reader including, for example:
    a receptacle (715) to receive a microplate (710) having at least one optical sensor;
    a radiation source (705) having a collimating lens (706), an incident beam (708), and a reflected beam (709);
    an image recorder (720); and
    an imaging lens or lens group, such as a pair of doublet lenses (shown as 730, 740) between the received microplate and the image recorder, the incident beam being oriented with respect to the optical sensor on the received microplate in the receptacle at an incident angle ($\theta_1$) of greater than about 45°, and the image recorder being oriented with respect to the reflected beam (709) at a reflected angle ($\theta_2$) of greater than about 5°. The reflected angle ($\theta_2$) as defined above, is the incident angle relative to the normal of the plane of the image recorder.

The reader can have a spatial resolution, for example, of from about 0.5 to about 1,000 micrometers, from about 1 to about 1,000 micrometers, from about 1 to about 100 micrometers, from about 1 to about 10 micrometers, and from about 5 to about 10 micrometers, including any intermediate ranges and values.

The apparatus can further comprise, for example, a microplate, a well plate, a microscope slide, a chip format, or like analyte container, support member, or sample presentation article, and optionally including, for example, microfluidic flow facility. In embodiments, the apparatus can have at least one microplate, having at least one well, the well having the at least one optical sensor therein, and the sensor having a signal region and an optional reference region. The microplate can be an array of wells such as commercially available from Corning, Inc.

The radiation source can be, for example, a light emitting diode (LED), and like low- or non-coherent light sources. Other radiation sources can be selected if desired and properly adapted to the disclosed apparatus and method. The radiation source can alternatively be or additionally include, for example, a fluorescent source capable of providing a fluorescent incident beam or fluorescence inducing incident beam.

In embodiments, the incident angle ($\theta_1$) can be, for example, from about 45° to about 70°, and the reflected angle ($\theta_2$) can be, for example, from about 5° to about 70°, including intermediate values and ranges. When the image to object magnification ratio is >1:1, then $\theta_1<\theta_2$. When the image to object magnification ratio is <1:1, then $\theta_1>\theta_2$. $\theta_2$ thus takes a wider range.

In embodiments, the radiation source (705) having a collimating lense (706) and incident beam (708) can further include, for example, a fluorescent filter (707), and like optical conditioning components. The effective size of the radiation source, such as an LED emitter, can be selected such that the angle spread of the nearly collimated beam is smaller than the resonance angle or cone angle (discussed below) of the sensor. In embodiments, the image recorder can be, for example, a CCD or CMOS camera, or like image recorder devices. A CCD having a very thin cover glass or no cover glass can provide improved image quality compared to a thick cover glass. The CCD or CMOS camera or like image recorder device can be, for example, free of a cover glass.

In embodiments, the received microplate can have a base or substrate thickness, for example, of from about 10 micrometers to about 10,000 micrometers, about 50 micrometers to about 10,000 micrometers, and 100 micrometers to about 1,000 micrometers, including any intermediate values and ranges. A specific example of a microplate base thickness is, for example, of from about 0.1 millimeters to about 10 millimeters, such as 0.3 millimeters to about 1.0 millimeters. A thinner microplate base can, for example, reduce distortion and can improve image quality. A thin microplate base can be, for example, glass or like material having a thickness of about 0.7 mm to 1.0 mm and is representative of the thicknesses found in certain commercial products. Glass or like material having a thickness of less than about 0.4 mm is operatively a thin base plate material.

In embodiments, the incident beam can contact at least one sensor in, for example, at least one of: a single well, two or more wells, a plurality of wells, or all wells of the received microplate.

In embodiments, the apparatus can be configured so that the incident beam contacts, irradiates, or excites, one or more sensors, in one or more wells in sequential or systematic scanning fashion (see for example commonly owned and assigned copending application U.S. Ser. No. 61/231,446).

In embodiments, the disclosure provides a method of reading an evansent wave sensor in the abovementioned apparatus having an engaged microplate having at least one sensor, comprising:
forming a microplate assembly by engaging the receptacle with a microplate having at least one well, the well having at least one sensor therein;
contacting the sensor at a first location with the incident beam at an incident angle ($\theta_1$) of greater than 45°; and
recording the image received from the contacted sensor with the image recorder, the image recorder being oriented with respect to the reflected beam at a reflected angle ($\theta_2$) of greater than about 5°.

The evanscent wave sensor can be, for example, a resonant waveguide biosensor, or like sensors, or a combination of such sensors.

The method can further comprise at least one relative moving (i.e., movement), of the microplate with respect to the incident beam to second location, and thereafter contacting at least one sensor of the microplate at the second location with the incident beam, and recording the image received with the image recorder. The relative moving of the microplate with respect to the incident beam can be accomplished by, for example, translating the beam stepwise, continuously, or a combination thereof, across the at least one sensor.

In embodiments, the sensor can include on its surface, for example, at least one of a live-cell, a bioentity, a chemical compound, a coating, and like entities, or a combination thereof.

The spatial resolution of the recorded image can be, for example, from about 0.5 to about 10 micrometers, including intermediate values and ranges, and the excellent spatial resolution can be sufficient to accomplish, for example, sub-cellular label-free imaging, and like imaging objectives.

In embodiments, the method can, for example, further comprise simultaneously or sequentially contacting the sensor with a fluorescence inducing incident beam and recording the received fluorescent image with a suitable recorder. That is, to accomplish, for example, cellular or sub-cellular fluorescence imaging (see, for example, commonly owned and assigned copending application U.S. Ser. No. 12/151,175, entitled "SYSTEM AND METHOD FOR DUAL-DETECTION OF A CELLULAR RESPONSE").

In embodiments, the disclosure provides a method for enhancing the spatial resolution of resonant waveguide sensor comprising, for example:
interrogating the sensor at an incident angle ($\theta_1$) of greater than 45°; and
recording the image received from the interrogated sensor with a suitable imager or like image recording device, the imager being oriented with respect to the reflected beam at a reflected angle ($\theta_2$) of greater than about 5°.

Spatial Resolution of Resonant Waveguide Grating Coupler (RWGC).

Figure 1:
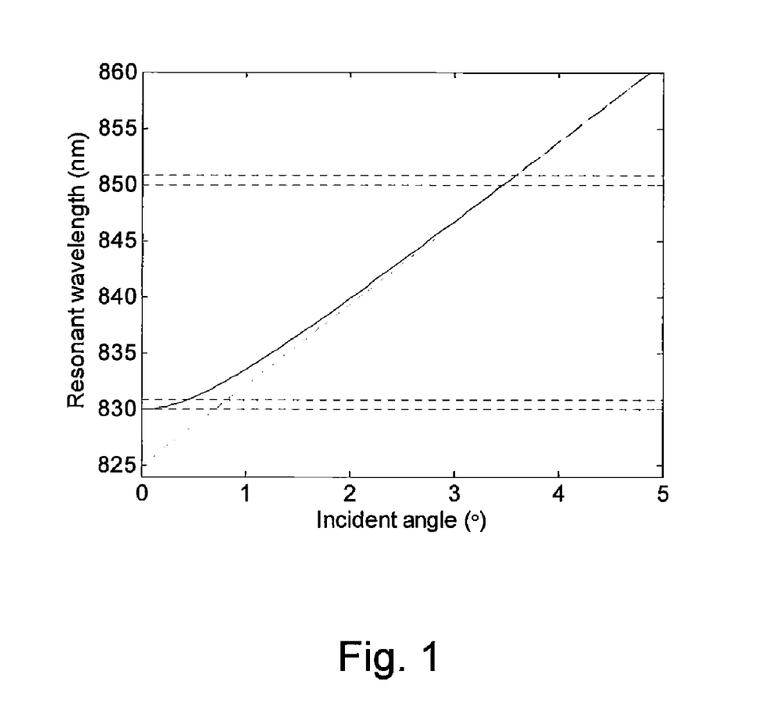
FIG. 1 shows, as background, a Rigorous Coupled Wave Analysis (RCWA) simulation of resonant wavelength as a function of the incident angle ($\theta$).

The Epic® sensor is a waveguide grating coupler. Resonant coupling occurs when the phase matching condition is satisfied:

$$\frac{\lambda}{\Lambda} \pm \sin\theta = n_{\it eff} \quad (1)$$

where $\theta_1$ is the incident angle, $\lambda$ the resonant wavelength, $\Lambda$ the grating pitch, and $n_{\it eff}$ the effective index of the waveguide. The plus sign represents the forward propagating leaky wave, and the negative sign for reverse propagating leaky wave. Given the grating structure and the waveguide material and thickness, the spectral profile of the resonance can be simulated using rigorous coupled wave analysis (RCWA). Simulation can be accomplished using, for example, G-Solver® (www.gsolver.com) or like diffraction grating simulation software. For Epic® sensors the grating pitch can be 500 nm, the depth can be 50 nm, and the thickness of the niobia waveguide can be 146 nm. RCWA simulation of the grating resonance wavelength as a function of incident angle is depicted in FIG. 1.

Physically, when light is incident on the grating, the free space wave is coupled into the leaky wave in the waveguide grating structure. The leaky wave coherently couples with the incident wave over a distance L.

Figure 2:
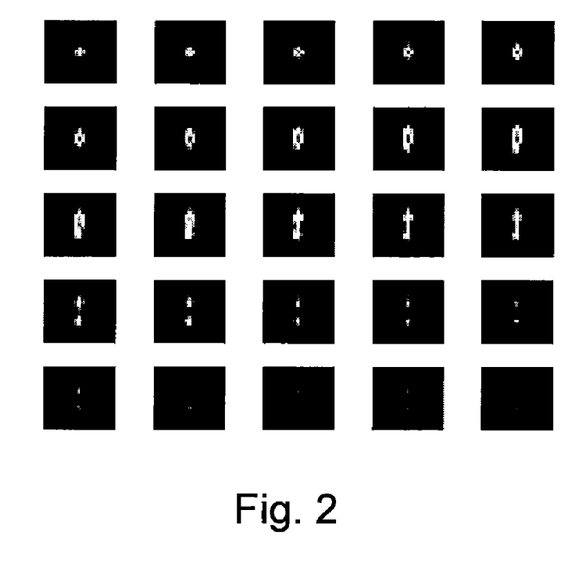
FIG. 2 shows, as background, wavelength-dependent images of a sensor grating when irradiated or excited by a 20 micrometer beam at normal incidence.

The relationship between resonance width and the spatial resolution can also be understood from the perspective of optical diffraction. The range of the resonance angle $\theta'$ at far field dictates that the image resolution is limited by diffraction (d):

$$d = 1.22 \frac{\lambda}{\Delta \theta'} \quad (2)$$

where $\Delta\theta'$ is the half width of the resonant angle (also known as the cone angle) and it can be numerically simulated through RCWA. Alternatively, the narrower the resonance angle, the more accurately the resonance angle (or wavelength) can be determined. Therefore there exists a tradeoff between detection sensitivity and the spatial resolution. The spectral width of the resonance is constant at a near normal incidence angle. Operating at the normal incident angle increases the numerical aperture (NA=n sin $\theta'$) considerably as illustrated in FIG. 1, where $\theta'$ is the width of the resonance angle. The dotted line is a linear approximation according to eq. (1). The solid line is a simulation result provided by RCWA theory. The point spread function of the grating sensor under normal incidence was directly measured in an experiment. A beam with the 20 micrometers waist diameter was located on the sensor surface. Spreading of the leaky wave was imaged as a function of wavelength within the resonance range. FIG. 2 confirmed that the leaky wave spreads over a distance of about ±50 micrometers. FIG. 2 shows that at resonance wavelength the leaky wave extends beyond +/−50 micrometers. The wavelength was varied from 829 nm to 831.5 nm at increments or intervals of 0.1 nm. An initial relatively small single beam spot (top left) transforms in the FIG. 2 frames going from left to right and steps (top to bottom) to a high resonance (middle row) condition, and then to little or no beam (bottom right). At a wavelength longer than the resonance, the high angle components of the beam continue to excite resonance. Although using a confocal detection scheme can improve the image resolution by two-fold, such a resolution remains insufficient to resolve an individual cell of most cell types.

To improve the spatial resolution, the sensor can be reconfigured to broaden the resonance width. This can be achieved, for example, through a deeper grating design, using 2D gratings, or like modifications.

Figure 3:
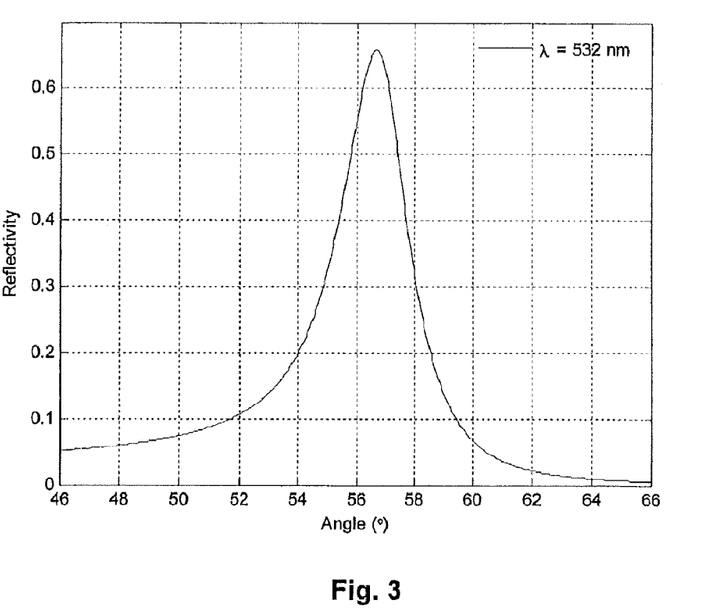
FIG. 3 shows the angular resonance of an Epic® sensor at 532 nm.
Figure 4:
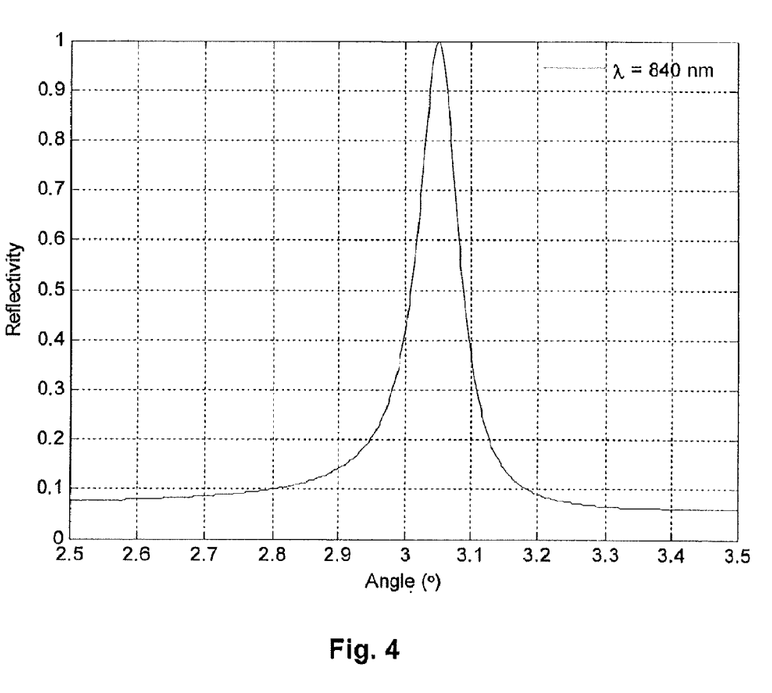
FIG. 4 shows angular resonance of an Epic® sensor at 840 nm.

However, an alternative approach can improve the spatial resolution of existing Epic® sensors and like sensors without any physical modification. In embodiments, it was discovered that instead of operating at near normal (e.g., $\theta_1=0°$) incident angle, use of a large incident angle interrogation approach enables a significantly increased numerical aperture. RCWA simulation of the angular resonance interrogated with a 532 nm wavelength beam is shown in FIG. 3, where the $1/e^2$ angular width is 8°. By comparison, the angular resonance at a near normal incidence angle is only 0.2°, as indicated in FIG. 4 at 840 nm. Taking into account the effect of incidence angle, the numerical aperture at 532 nm is boosted by a factor of 24 compared to near normal incidence. By further considering the difference in wavelength, the spatial resolution at 532 nm is estimated to be about 5.8 millimeters, which is about thirty-eight (38) times smaller than that at 840 nm. This resolution is substantially smaller than the size of typical cells, hence making single cell resolution label free imaging feasible with a standard Epic® sensor.

Although the peak grating resonance reflectivity is reduced to about 70%, this is more than compensated for by the enhanced quantum efficiency of CCD cameras at visible wavelengths. The reduced leaky wave propagation distance is due to the enhanced coupling by the grating at large incident angles. Operating at a shorter wavelength can further improve the resolution.

The surface wavelength interrogation sensitivity (WIS) is simulated to be 0.27 nm/nm, which is slightly larger than that at 830 nm due to a shorter penetration depth. The sensor can also be interrogated in transverse electric (TE) mode (i.e., s-polarized) at large incident angle using visible wavelengths, the surface WIS is substantially lower than that of transverse magnetic (TM) mode (i.e., p-polarized) (see for example commonly owned and assigned copending U.S. Provisional Application Ser. No. 60/668,908, or published PCT application WO06/108183). These documents are hereby incorporated by reference in their entirety.

Although the sensor can be interrogated using swept wavelength imaging technique, a simpler intensity imaging technique which is commonly used in SPR imaging can be employed because of the wide resonance width. This method can be facilitated by the use of a low coherence light source, which removes the parasitic interference fringes (see for example commonly owned and assigned copending copending U.S. Ser. No. 61/259,802) This document is hereby incorporated by reference in its entirety.

Figure 5:
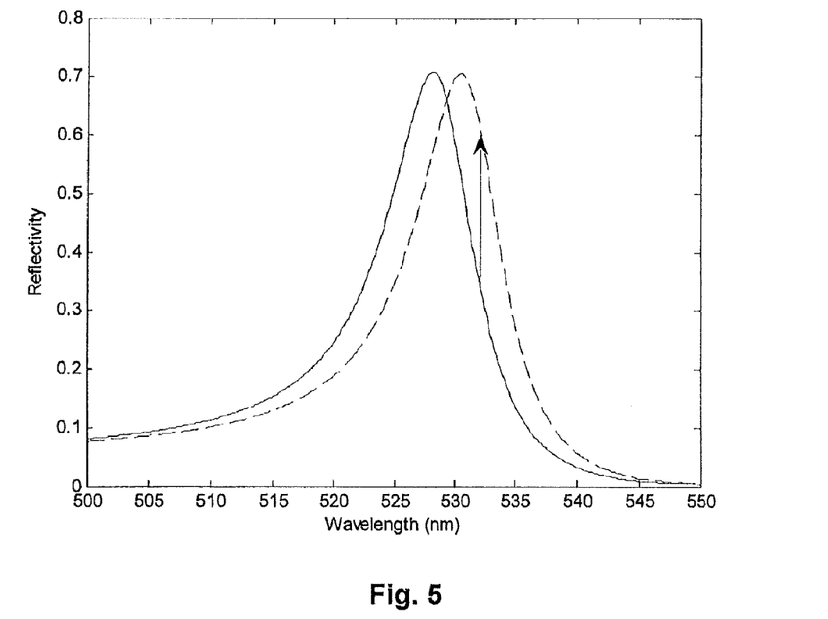
FIG. 5 shows a simulation of a wavelength shift in spectral resonances of an Epic® sensor at an incident angle of 57.9° before binding (solid line) and after binding (dashed line) of a 10 nm thick simulated bio-layer.

FIG. 5 shows a simulation of a wavelength shift (i.e., a dark field image) in spectral resonances of an Epic® sensor at an incident angle of 57.9° before binding (solid line) and after binding (dashed line) of a 10 nm thick simulated bio-layer. The simulated bio-layer having an index of refraction of about 1.5 that resembles, for example, a cell construct or a protein mixture. By fixing the interrogation wavelength (solid line) at the negative slope (up arrow) of the sensor resonance, a shift of sensor resonance induced by surface mass increase is manifested as an increase of sensor reflectivity (dashed line). By optimizing the operating wavelength the sensor can cover a dynamic range of about 5 nm. This operating mode is similar to dark field microscopy.

Figure 6:
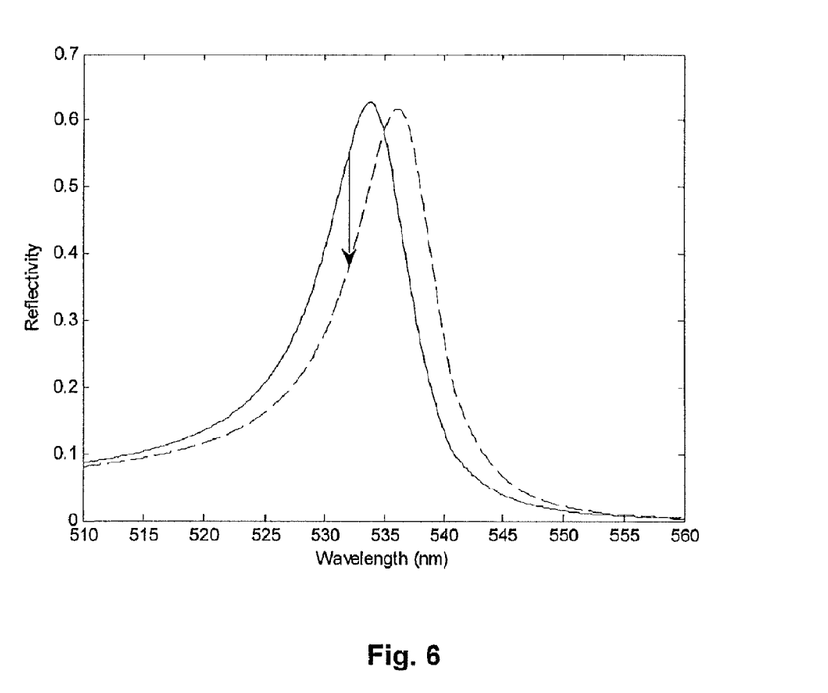
FIG. 6 shows a wavelength shift in spectral resonances of an Epic® sensor at an incident angle of 56° before binding (solid line) and after binding of a 10 nm thick bio layer.

FIG. 6 shows an alternative operating point on the positive slope (down arrow) of the resonance where an increase of surface mass causes the grating reflectivity to decrease (dashed line). This operating mode is similar to light field mode image or bright field microscopy.

In both instances, the simulated mass increase was a 10 nm thick bio-layer which is similar to the effect of cell attachment. For a conventional Epic® assay this corresponds to a wavelength shift of about 2.4 nm. The intensity change in dark field mode is over 80%. Using a CCD camera with 100 frames per second (fps) frame rate, the relative intensity of noise per pixel is about 0.001 $Hz^{-1/2}$. This corresponds to an Epic® equivalent noise of about 3 pm $Hz^{-1/2}$. Such a noise level is comparable to swept wavelength imaging instrument and is sufficient for cell assays.

Defects on the grating can be distinguished using both dark-field and bright field imaging.

Various imaging methods can be used to acquire the images. These include full field imaging using for example, a 2D image sensor, raster scanning, line scanning, or like methods. The following example demonstrates high resolution imaging using a CCD camera.

EXAMPLES

The following examples serve to more fully describe the manner of using the above-described disclosure, as well as to further set forth the best modes contemplated for carrying out various aspects of the disclosure. It is understood that these examples do not limit the scope of this disclosure, but rather are presented for illustrative purposes. The working examples further describe how to make and use the apparatus and methods of the disclosure.

Example 1

Demonstration of High Resolution Label-Free Imaging

An optical imaging system as shown in FIG. 7A provides a 1:1 image of a single optical sensor (not shown) within a microplate (710) onto a CCD (720) camera (Point GREY Research, Dragonfly Express). An imaging lens or lens group, such as the pair of doublet lenses (730, 740), can have a focal length of, for example, about 50 mm. The CCD pixel size was 7.4×7.4 micrometers. Because of the large incident angle of the object plane of the microplate, conventional imaging results in a very narrow in-focus field of view. In this example the CCD plane was tilted to bring the entire field of view into focus. This is also known as the Scheimpflug camera configuration. Aberration of the system is mainly due to the cover glass of the CCD and the thickness of the grating sensor substrate. Aberrations can be corrected and image quality improved by, for example, lens design or by removing the CCD cover glass, reducing the grating substrate thickness, or a combination thereof. FIG. 7B shows in perspective view an exemplary prior art microplate (710), or like support member, having one or more sensors. The multiwell plate (710) (e.g., microplate) includes a peripheral skirt 12 and a top surface 14 having an array of wells 16 each of which is capable of receiving an aliquot of sample to be assayed. The multiwell plate (710) conforms to industry standards for multiwell plates. The multiwell plate (710) can have, for example, ninety-six wells in 16 in an 8×12 matrix, and like well formats, such as 12, 96, 386, etc. In addition, the height, length, and width of the multiwell plate (710) can conform to industry standards. However, the present disclosure can be implemented in a multiwell plate that has any number of wells and is not limited to any specific dimensions and configurations. The bottom of each well of the plate can include one or more sensors which can be exposed to a incident beam of radiation through the transpent base or bottom of the plate (not shown).

The light source is a true green LED (Osram). The center wavelength is 527 nm and the spectral FWHM is 33 nm. A standard fluorescent filter with center wavelength of 532 nm and pass band of 2 nm is used to filter the collimated output from the LED. The incident angle of about 58° was selected to operate in the dark field mode. The fluorescent filter can be angle tuned to shift the transmission toward a shorter wavelength (e.g., by about 30 nm) and switch the system into bright field mode.

Figure 8A:
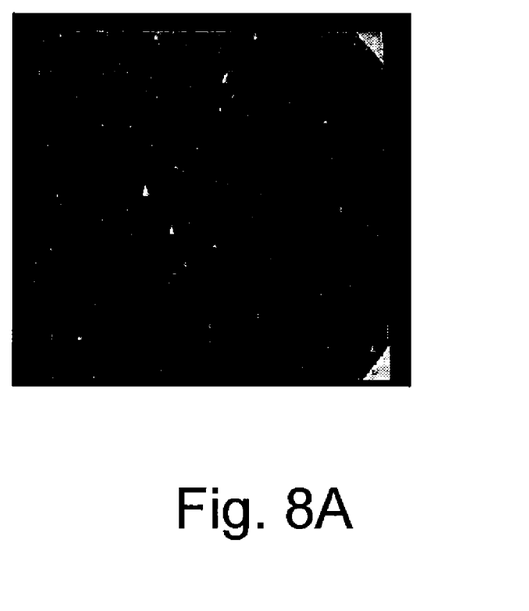
FIGS. 8A and 8B show, respectively, LH60 cells on an Epic® sensor that are imaged in dark field mode and bright field mode.
Figure 8B:
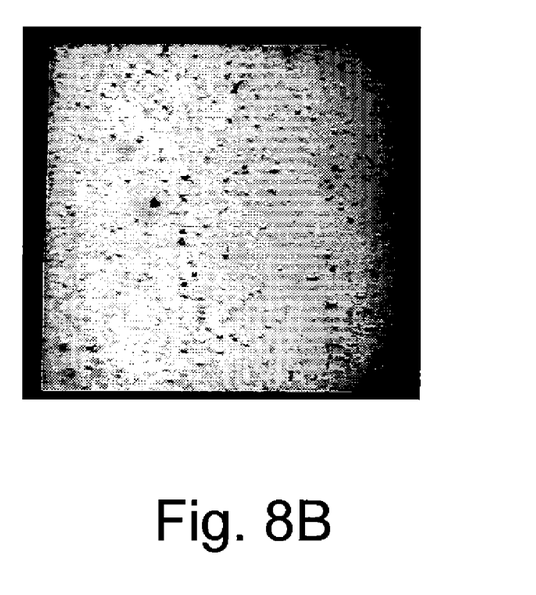

Low density HL60 cells which have a nearly individual cell size of about 10 micrometers were imaged in the disclosed system in both dark field and bright field modes. The dark field and bright field images are shown and compared in FIGS. 8A and 8B, respectively. The bright spots (FIG. 8A) and dark spots (FIG. 8B) can be correlated between the images, indicating that they are caused by cell attachment. The magnitude of intensity change was in good agreement with the simulation. Slight distortion of the image is inherent to the Scheimpflug imaging configuration. The image intensity can be corrected on a line-by-line basis, if desired, to balance the background intensity.

Figure 9:
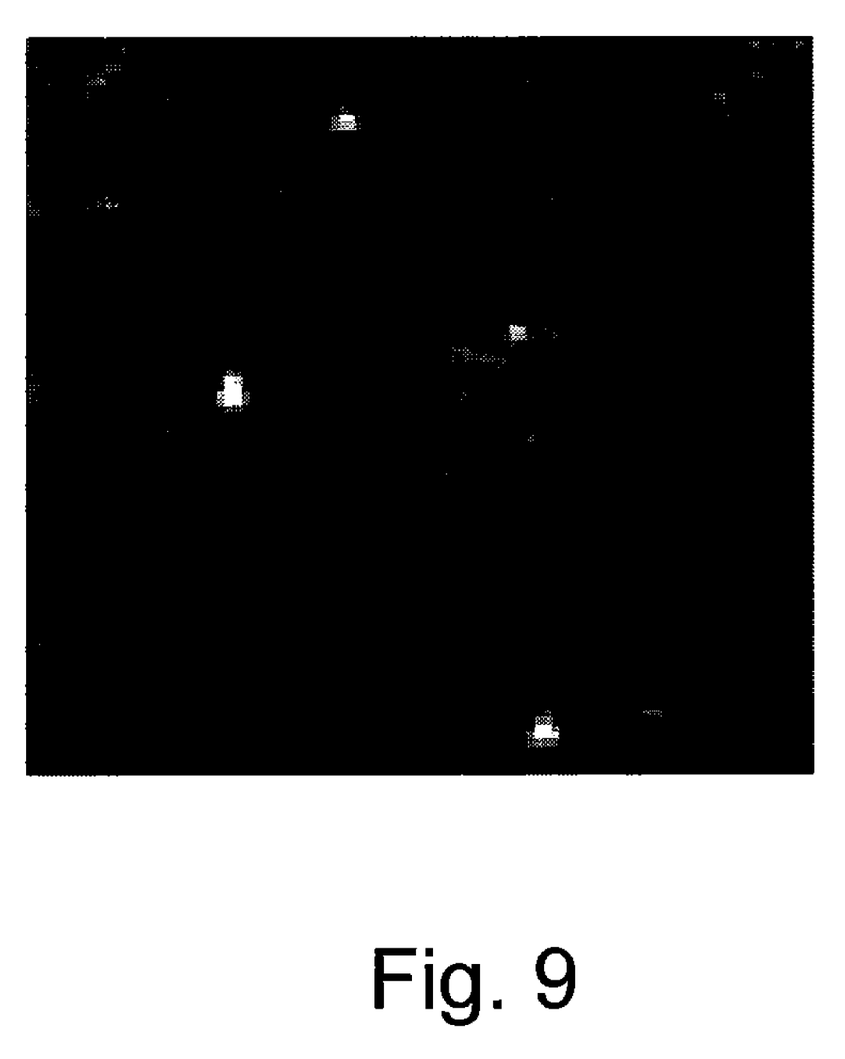
FIG. 9 shows low density LH60 cells imaged in dark field mode showing approximate single pixel resolution.

The image quality can be affected by astigmatism that can be caused by the CCD cover glass. The image focus can be optimized in the y direction, which is the grating leaky wave propagation direction. FIG. 9 shows low density LH60 cells imaged in dark field mode showing approximate single pixel resolution. The single pixel resolution capability was demonstrated and shown in FIG. 9, which suggests a spatial resolution of about 7.4 micrometers.

In embodiments, the disclosed imaging technique can be applied to compact Epic® configurations and applications by, for example, redesigning the field of view to cover 4×3 well-plate configurations, or like configurations. In embodiments, the disclosed system provides high spatial resolution and at reduced cost because the disclosed system can avoid a precision swept wavelength mechanism. The system's overall simplicity provides an optical reader having lower overall cost. However, in this operating mode the readout can be more sensitive to defects on the sensor surface.

The use of a visible wavelength source as in the disclosed system can further facilitate combination of label free imaging capability with fluorescence imaging functions (see for example commonly owned and assigned copending U.S. Ser. No. 12/151,179, filed May 5, 2008, entitled "SYSTEM AND METHOD FOR DUAL-DETECTION OF A CELLULAR RESPONSE").

The disclosure has been described with reference to various specific embodiments and techniques. However, it should be understood that many variations and modifications are possible while remaining within the scope of the disclosure.

What is claimed is:

1. An apparatus for label free imaging comprising:
an optical reader comprising:
a receptacle to receive a microplate having at least one optical sensor;
a radiation source comprising a light emitting diode having a collimating lens, an incident beam, and a reflected beam;
an image recorder; and
an imaging lens between the received microplate and the image recorder, the incident beam being oriented with respect to the optical sensor on the received microplate in the receptacle at an incident angle ($\theta_1$) of from about 45° to about 70°, and the image recorder being oriented with respect to the reflected beam at a reflected angle ($\theta_2$) of from about 5° to about 70°, wherein the reader has a spatial resolution from about 0.5 to about 100 micrometers.

2. The apparatus of claim 1 further comprising a microplate having at least one well or chamber, the well or chamber having the at least one optical sensor therein, the sensor having a signal region and an optional reference region, and the well or chamber optionally having microfluidic flow facility.

3. The apparatus of claim 1 wherein the image recorder is a CCD or CMOS camera.

4. The apparatus of claim 3 wherein the CCD or CMOS camera is free of a cover glass.

5. The apparatus of claim 1 wherein the received microplate has a base thickness of from about 10 micrometers to about 10,000 micrometers.

6. The apparatus of claim 1 wherein the incident beam contacts at least one sensor in at least one of: a single well, two or more wells, a plurality of wells, or all wells of the received microplate.

7. The apparatus of claim 1 wherein the radiation source further comprises a fluorescent source having a fluorescent incident beam and a fluorescent image recorder.

8. A method of reading an evansent wave sensor in a label free apparatus, the apparatus comprising:
an optical reader comprising:
a receptacle to receive a microplate having at least one optical sensor;
a radiation source comprising a light emitting diode having a collimating lens, an incident beam, and a reflected beam;
an image recorder; and
an imaging lens between the received microplate and the image recorder, the incident beam being oriented with respect to the optical sensor on the received microplate in the receptacle at an incident angle ($\theta_1$) of from about 45° to about 70°, and the image recorder being oriented with respect to the reflected beam at a reflected angle ($\theta_2$) from about 5° to about 70°, the microplate having at least one well or chamber, the well or chamber having the at least one optical sensor therein, the sensor having a signal region and an optional reference region, and the well or chamber optionally having microfluidic flow facility;
the method comprising:
forming a microplate assembly by engaging the receptacle with a microplate having at least one well, the well having at least one sensor therein;

contacting the sensor at a first location with the incident beam at an incident angle ($\theta_1$) of from about 45° to 70°;

recording the image received from the contacted sensor with the image recorder, the image recorder being oriented with respect to the reflected beam at a reflected angle ($\theta_2$) of from about 5° to 70°; and at least one relative moving of the microplate with respect to the incident beam to a second location, and thereafter contacting at least one sensor of the microplate at the second location with the incident beam, and recording the image received.

9. The method of claim 8 wherein the at least one relative moving of the microplate with respect to the incident beam comprises translating the beam stepwise, continuously, or a combination thereof, across the at least one sensor.

10. The method of claim 8 wherein the sensor includes on its surface at least one of a live-cell, a bioentity, a chemical compound, a coating, or a combination thereof.

11. The method of claim 8 wherein the spatial resolution of the recorded image is from about 0.5 micrometer to about 10 micrometers, and is sufficient for sub-cellular label-free imaging.

12. The method of claim 8 further comprising contacting the sensor with a fluorescent incident beam and recording the received fluorescent image.

13. A method for enhancing the spatial resolution of resonant waveguide sensor comprising:

interrogating the sensor at an incident angle ($\theta_1$) of from about 45° to 70°; and recording the image received from the interrogated sensor with an image recorder, the image recorder being oriented with respect to the reflected beam at a reflected angle ($\theta_2$) of from about 5° to 70°.

* * * * *